(12) United States Patent
Yamazaki et al.

(10) Patent No.: US 7,020,592 B2
(45) Date of Patent: Mar. 28, 2006

(54) METHOD OF ANALYZING CHEMICAL PROCESSES

(75) Inventors: Yasuo Yamazaki, Tokyo (JP); Hamp Turner, Morris Plains, NJ (US)

(73) Assignees: Nippon Chemical Industrial Co., Ltd., Tokyo (JP); Oli Systems, Inc., Morris Plains, NJ (US)

( * ) Notice: Subject to any disclaimer, the term of this patent is extended or adjusted under 35 U.S.C. 154(b) by 743 days.

(21) Appl. No.: 10/181,958

(22) PCT Filed: Mar. 22, 2001

(86) PCT No.: PCT/JP01/02299

§ 371 (c)(1),
(2), (4) Date: Aug. 2, 2002

(87) PCT Pub. No.: WO01/71531

PCT Pub. Date: Sep. 27, 2001

(65) Prior Publication Data

US 2003/0004696 A1   Jan. 2, 2003

(30) Foreign Application Priority Data

Mar. 22, 2000   (JP) .............................. 2000-080752

(51) Int. Cl.
*G06F 15/00* (2006.01)
*G06F 17/10* (2006.01)
(52) U.S. Cl. ............................... 703/2; 703/6; 715/504
(58) Field of Classification Search .................... 703/2, 703/6; 715/504
See application file for complete search history.

(56) References Cited

U.S. PATENT DOCUMENTS 5,893,123 A * 4/1999 Tuinenga .................... 715/504

OTHER PUBLICATIONS

Thomas R. Holm, et al., "Computing SI and CCPP Using Spreadsheet Programs" vol. 90, No. 7, Jul. 1998, pp. 80-89.
Bhairav D. Joshi, "Spreadsheet Templates for Chemical Equilibrium Calculations" vol. 13, No. 1, 1994, pp. 101-123.
Anton J. Pintar et al., "Process Simulation and Control Center: An automated Pilot Plant Laboratory", vol. 6, No. 3, 1998, pp. 145-150.
Glen Hopkinson, "Desktop Chemical Data Analysis: Meeting the Needs of Discovery Scientists", Proceedings of the 1994 Chemical Information Conference, Annecy, France, pp. 129-134.

* cited by examiner

*Primary Examiner*—Hugh Jones
(74) *Attorney, Agent, or Firm*—Armstrong, Kratz, Quintos, Hanson & Brooks, LLP

(57) ABSTRACT

When chemical process conditions and chemical species are input on a spreadsheet software (1), a chemical model is selected according to the chemical species by a software (4, 5, 6) different from the spreadsheet software (1), thermodynamic property data for the chemical model is generated, and a chemical equilibrium is evaluated based on this data. The chemical equilibrium is simulated on the spreadsheet software (1) based on this evaluation result, and the simulation result is displayed on the spreadsheet software (1).

10 Claims, 7 Drawing Sheets

METHOD OF ANALYZING CHEMICAL PROCESSES

FIELD OF THE INVENTION

The present invention relates to a method of analyzing chemical processes.

BACKGROUND OF THE INVENTION

Although chemical reactions, especially reactions of chemicals in an aqueous solution, have been investigated for many years, the reactions performed are not necessarily simple even when reacting pure chemical substances together, and especially when one or more chemical substance is a weak electrolyte. It is not easy to analyze such reactions correctly.

In an industrial process, since there are often impurities present, this problem becomes still more complicated. OLI Systems, Inc., at which one of the Inventors works, has been tackling this problem for many years, and has proposed that it should be possible to calculate thermodynamic properties for all substances having known species by using a program and support data base with a computer. In this computer system, the amount of species in the aqueous solution at a thermodynamic equilibrium state can be calculated. Chemical processes or devices are designed using this calculation result.

Process control details and control results are often manipulated, displayed and recorded using a "Distributed Control System (DCS)." However, software is specific to system manufacturers, hardware may also be specific, and it is difficult to link up with other systems.

SUMMARY OF THE INVENTION

However, by using software such as PI DATALINK which OSI Software Inc. developed, the data stored on the DCS can now be displayed on Microsoft's spreadsheet software, Excel.

Chemical reactions in aqueous solution have been intensively studied for a long time, and it is now known that other chemicals besides the main chemicals participate therein. Which chemical substances are produced from which precursors, and the values of their activity coefficients, are questions which are being studied worldwide, and the results are being entered into databases. Some software which uses these databases to calculate the thermodynamic properties of chemical species considered likely under predetermined conditions, for example, concentration, temperature and pressure, is also on the market.

However, the use of such software is not so widespread in the industrial sphere. One reason is because, even if a chemical process is simulated under predetermined conditions with such software, the simulation results can differ greatly from actual measurement data and there are no practical tools to help resolve the differences. Another reason is that, as the analysis results can not be displayed on software such as commercial spreadsheet software, users can not make more use of them as a useful source of information.

It is therefore an object of this invention to provide a method of analyzing chemical processes wherein chemical process parameters can be input on a spreadsheet software, the results of simulations of chemical equilibria based on the parameters can be displayed on the spreadsheet software, and chemical processes can be predicted and apparatus designed from the analyzed data.

In order to achieve the above object, this invention provides a chemical process analysis method comprising the steps of inputting a chemical process condition and chemical species on a spreadsheet software, evaluating a chemical equilibrium based on the input chemical process condition and chemical species by a software different from the spreadsheet software, simulating the chemical equilibrium on the spreadsheet software based on the evaluation results, and displaying the results of the simulation on the spreadsheet software.

The details as well as other features and advantages of this invention are set forth in the remainder of the specification and are shown in the accompanying drawings.

DESCRIPTION OF THE PREFERRED EMBODIMENTS

In the chemical process analysis method according to this invention, parameters (chemical process conditions and chemical species) required to select and extract a chemical model are input on a spreadsheet software, the input parameters are transferred to other software which evaluates chemical equilibria different from the spreadsheet software, a chemical equilibrium is evaluated by the chemical equilibrium evaluating software based on these parameters, the evaluation results are again transferred to the spreadsheet software, the chemical equilibria are simulated on the spreadsheet software, and the results of the simulation are displayed on the spreadsheet software.

"Evaluation of chemical equilibria" means that characteristic values are calculated for a chemical model, and that equilibrium conditions and the chemical composition in the system are determined.

Hereafter, this invention will be described referring to the appended drawings.

First Embodiment

Figure 1:
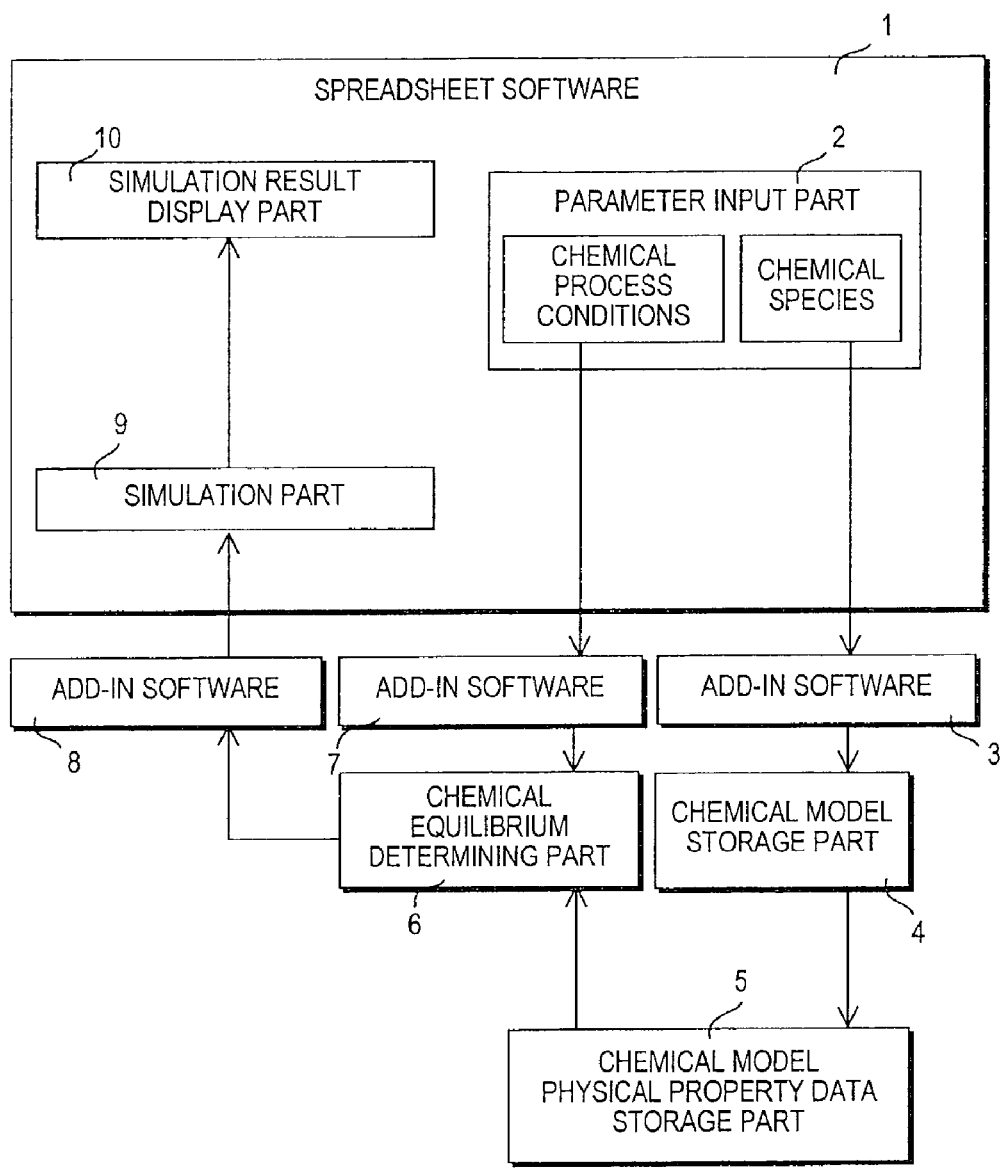
FIG. 1 is a schematic view showing an analysis system using the method of analyzing chemical processes according to the first embodiment of this invention.
Figure 2:
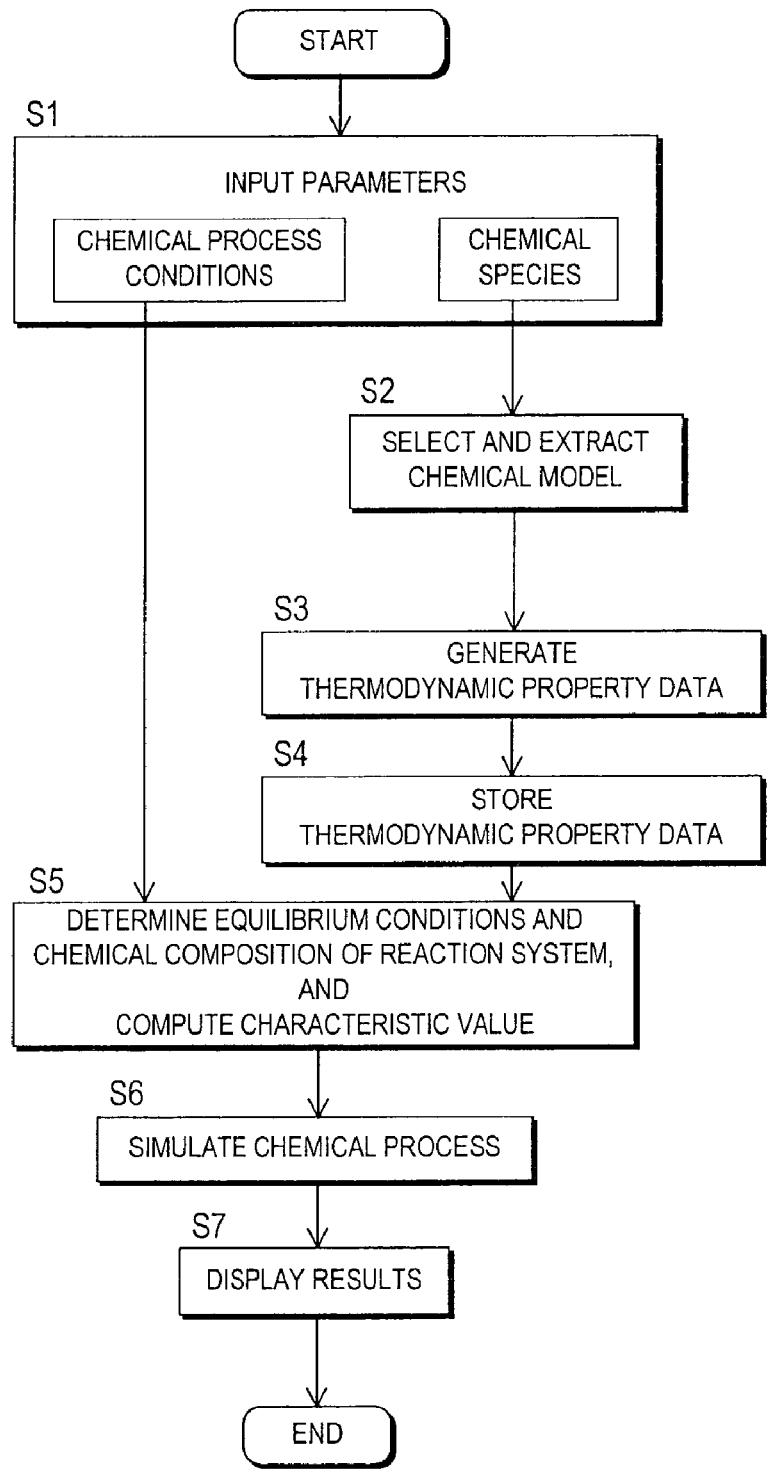
FIG. 2 is a flowchart describing the use of the analysis system.

FIG. 1 is a schematic view showing the first embodiment of this invention, and FIG. 2 shows a flowchart of the operations performed.

A spreadsheet software 1 is preferably Excel, which is Microsoft's spreadsheet software. It is preferable that Excel is version 5.0 or higher, and that the operating system is Windows 95 or higher which is Microsoft's operating system (OS).

The spreadsheet software 1 comprises a parameter input part 2, simulation part 9 and simulation result display part 10. Blocks 3–8, appearing outside the block showing the spreadsheet software 1, show software other than the spreadsheet software 1 or a database (identical for FIG. 3, FIG. 4 hereafter).

In the parameter input part 2, chemical process conditions and chemical species can be input from a keyboard, not shown (step S1). "Chemical process conditions" are conditions such as concentration, temperature, pressure, pH, bubble point, enthalpy, dew point and solubility limit, one or more of these conditions being input.

The term "chemical species" represents initial chemical substances comprising a chemical model, for example $H_2O$, NaOH, HCl, $CO_2$, $H_2S$, $NH_3$ and $FeCl_3$, usually being input as chemical formulae.

The input chemical process conditions are sent to a chemical equilibrium determining part 6 through an add-in software 7. The input chemical species are also sent to a chemical model storage part 4 through an add-in software 3. "Add-in software" is software which can define special commands for adding special functions to the spreadsheet software 1.

In the chemical model storage part 4, all the standard chemical models are stored with reference to values in the literature, and the selection and extraction of chemical models according to the input chemical species are performed by an operating mechanism (step S2). "Chemical model" means all the chemical reactions that the input chemical species could induce, and all the chemical substances including intermediates resulting therefrom.

The chemical model storage part 4 comprises the following four parts (a)-(d).

(a) A list of initial chemical substances concerning a chemical process.

(b) A list of chemical substances which result from the chemical substances in (a) when these are in aqueous solution.

(c) Equations for the chemical reactions which may occur between the chemical substances in (b).

(d) A list of the chemical substances contained in (b) and the equations contained in (c).

More specifically, the "list of initial chemical substances concerning a chemical process" in (a) is a tabular list of the initial chemical substances from which a reaction system can be built, such as, for example, $H_2O$, NaCl, $Na_2CO_3$, $NH_3$, $HNO_3$ and $FeCl_3$, or any subset of these.

The "list of chemical substances which result from chemical substances in (a) when these are in aqueous solution" are the chemical substances which result from the various reactions, disassociations, and recombinations of the chemical substances in (a). As a short example, taking only $H_2O$ and NaCl as initial chemical substances, the following chemical substances would result: $H_2O_{aq}$, $HCl_{aq}$, $H^+$, $OH^-$, $Na^+$, $Cl^-$, $H_2O_{vap}$, $HCl_{vap}$, $NaOH.1H_2O$, $NaCl_{ppt}$, and $NaOH_{ppt}$. Other lists of initial chemical substances would result in a different list in (b). "Equations for the chemical reactions which may occur between the chemical substances in (b)" are chemical reaction equations which define the relationships between the chemical substances in (b). For example using $H_2O$ and NaCl as initial chemical species and the resulting list in (b) the following chemical reaction equations are contained in (c):

| | |
|---|---|
| $H_2O_{aq}$ = | $H^+ + OH^-$, |
| $H_2O_{vap}$ = | $H_2O$, |
| $HCl_{aq}$ = | $H^+ + Cl^-$, |
| $HCl_{vap}$ = | $HCl_{aq}$, |
| $NaCl_{ppt}$ = | $Na^+ + Cl^-$, |
| $NaOH.1H_2O$ = | $Na^+ + OH^- + H_2O$, |
| $NaOH_{ppt}$ = | $Na^+ + OH^-$. |

The "list of the chemical substances contained in (b) and the equations contained in (c)", is a list of all the list chemical substances in (b) and all the chemical reaction equations in (c). For example, using $H_2O$ and NaCl as initial chemical species the following list results:

$H_2O_{aq}$) $HCl_{aq}$, $H^+$, $OH^-$, $Na^+$, $Cl^-$, $H_2O_{vap}$, $HCl_{vap}$, $NaOH.1H_2O$, $NaCl_{ppt}$, $NaOH_{ppt}$,

| | |
|---|---|
| $H_2O_{aq}$ = | $H^+ + OH^-$, |
| $H_2O_{vap}$ = | $H_2O$, |
| $HCl_{aq}$ = | $H^+ + Cl^-$, |
| $HCl_{vap}$ = | $HCl_{aq}$, |
| $NaCl_{ppt}$ = | $Na^+ + Cl^-$, |
| $NaOH.1H_2O$ = | $Na^+ + OH^- + H_2O$, |
| $NaOH_{ppt}$ = | $Na^+ + OH^-$. |

In the chemical model storage part 4, a chemical model is determined from all the chemical reactions which could be induced by the input chemical species, and all the chemical substances including intermediates resulting therefrom.

The determined chemical model is sent to a chemical model physical property data storage part 5. The chemical model physical property data storage part 5 supplies basic conditions to the chemical model extracted, generates thermodynamic property data for the chemical model required to calculate characteristic values, equilibrium conditions and chemical components in the system (step S3), and stores this data (step S4). The "basic conditions" refer to conditions such as temperature, pressure and concentration, and a list of thermodynamic properties is generated according to variations in these conditions. The thermodynamic property data include activity coefficients, equilibrium constants, fugacity coefficients, stoichiometry constants, ionic valencies, critical characteristics, heat capacities and parameters required to determine them.

The generated thermodynamic property data are sent to the chemical equilibrium determining part 6. Based on the thermodynamic property data, the chemical equilibrium determining part 6 calculates characteristic values, determines equilibrium conditions and determines the chemical composition of the reaction system (step S5).

Specifically, characteristic values such as for example pH values, bubble points, saturation solubilities and boiling points are computed by an operating mechanism from the input chemical process conditions and the generated thermodynamic property data. Further, the chemical composition under various conditions is also assessed and determined, such as the composition of the reaction system at a predetermined pH, composition of the reaction system at a predetermined temperature, composition of the reaction system under adiabatic conditions, and composition of the reaction system at the saturation solubility.

The analysis results for characteristic values, equilibrium conditions and chemical composition of the reaction system are transferred to the spreadsheet software 1 via an add-in software 8. A simulation of the chemical process is performed using an operating mechanism on a simulation part 9 of the spreadsheet software 1 (step S6), and the results are displayed on the spreadsheet software 1 (step S7). The results of the simulation may for example be a display of temperatures, pressures, pH, concentrations and compositions of the reaction system by single point or multipoint. In particular, the simulation results may be displayed as a graph in a multipoint display.

Second Embodiment

Figure 3:
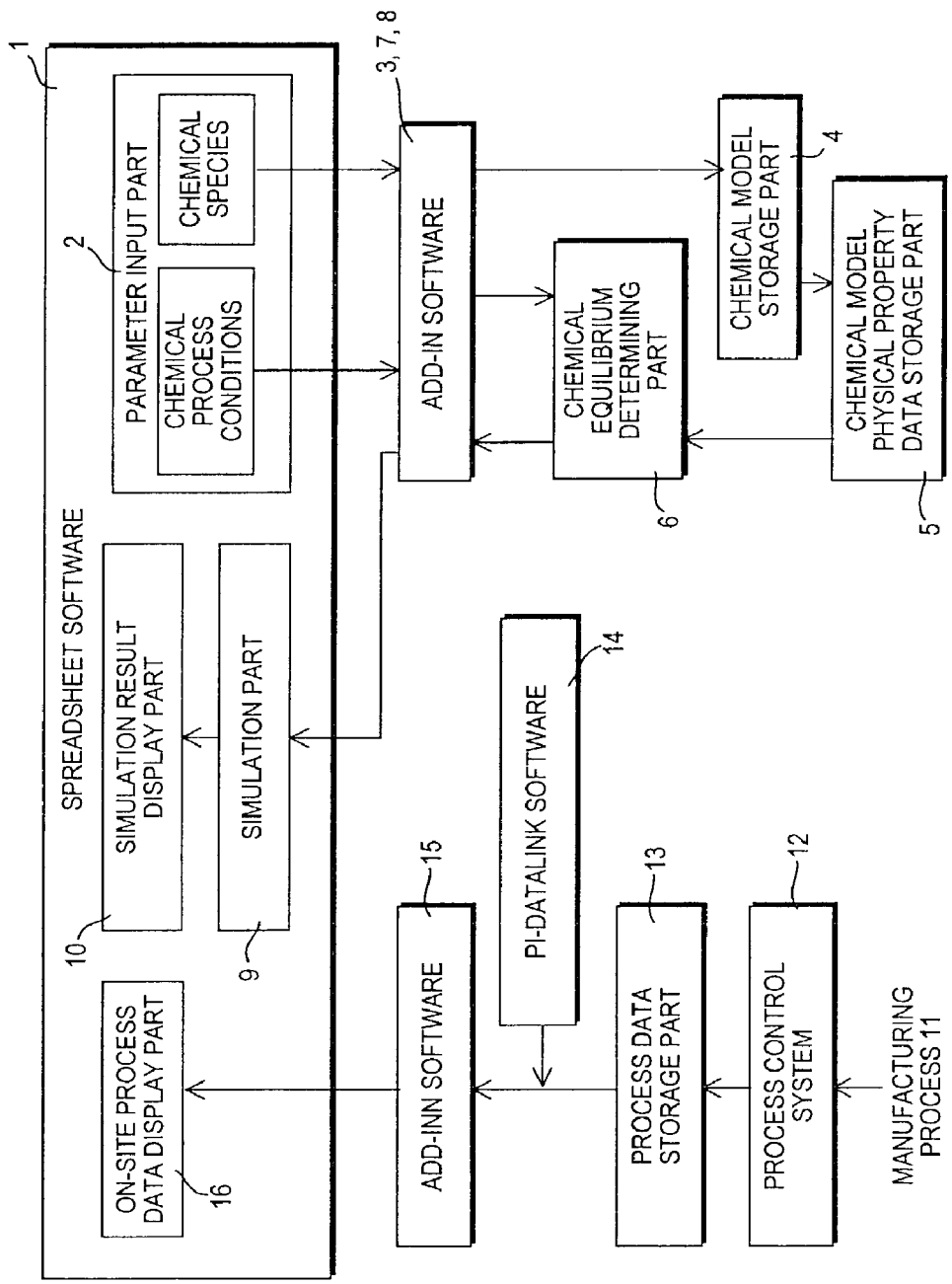
FIG. 3 is similar to FIG. 1, but showing a second embodiment of this invention.

FIG. 3 shows a second embodiment. This analysis system, in addition to the analysis system shown in FIG. 1, further comprises an on-site process data display part 16 which stores on-site process data from a production facility, and displays it on the spreadsheet software 1.

The spreadsheet software 1, in addition to the parameter input part 2, the simulation part 9 and the simulation result display part 10, further comprises the on-site process data display part 16.

A process control system 12 is connected to a manufacturing process 11, and manages process data at the production facility (factory) such as temperature conditions, concentration conditions, pressure conditions and pH conditions on a computer. The process data is transferred to a process data storage part 13, where it is stored.

The process data storage part 13 displays the process data at the production facility on the spreadsheet software 1 via the OS and an add-in software 15 by commercial software 14 such as, for example, PI-DATALINK (OSI Software Inc.). The process data displayed on the spreadsheet software 1 may for example be temperature, pressure, concentration and pH.

In this analysis system, a simulation of the chemical process can also be performed based on the process data by transferring the data on the spreadsheet software 1 to the parameter input part 2 by an operating mechanism.

Third Embodiment

Figure 4:
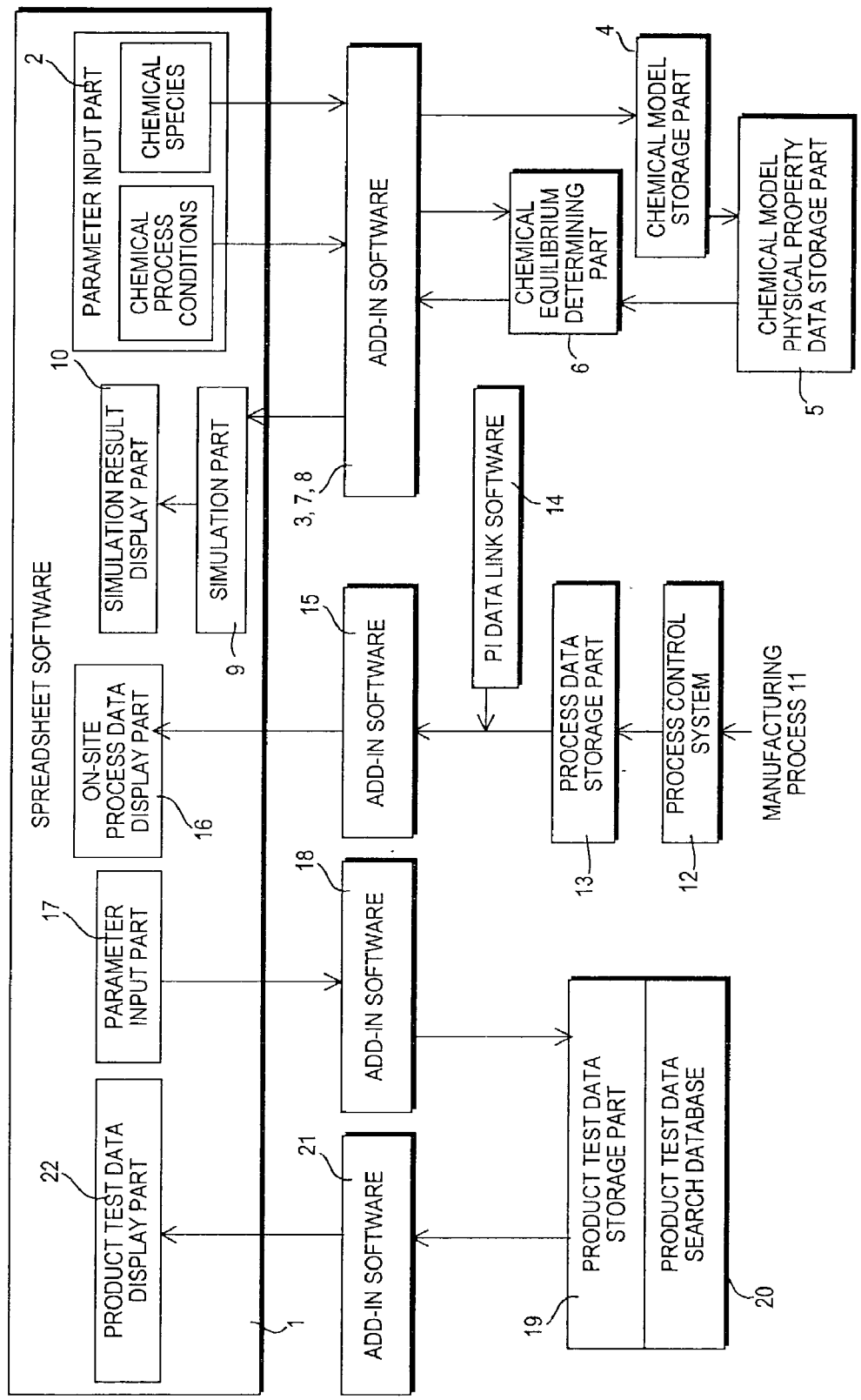
FIG. 4 is similar to FIG. 2, but showing a third embodiment of this invention.

FIG. 4 shows a third embodiment. This analysis system, in addition to the analysis system shown in FIG. 1 and FIG. 3, further comprises a product test data storage part 19 which stores test results for manufactured products or intermediate products in process of manufacture, and a product test data display part 22 which displays the product test data on the spreadsheet software 1.

The spreadsheet software 1 comprises the parameter input part 2, the simulation part 9 and the simulation result display part 10, and further comprises a parameter input part 17 for inputting parameters required to search test data for each product, and a product test data display part 22 for displaying the results. It still further comprises the process data display part 16 described in the second embodiment.

In the parameter input part 17 for inputting parameters required to search product test data for each product, product lot numbers, product names, client names, manufacturing dates and production facilities are input from a keyboard, for example. By inputting the required parameters, the product test data storage part 19 can be accessed via an add-in software 18.

In the product test data storage part 19, product specifications, product test data for products which have passed or failed, test record numbers, client names, manufacturing dates, production batch numbers and test records may for example be stored.

The product test data storage part 19 comprises a product test data search database 20 which can search product test results in relation to test record numbers, product names, client names, manufacturing dates and production facilities. In the product test data search database 20, searches are performed based on parameters input on the spreadsheet software 1, and corresponding data is displayed by the product test data display part 22 on the spreadsheet software 1 via an add-in software 21.

The items displayed by the product test data display part 22 may for example be test data for each product test result, test data for each production lot, test data for each client, and test data for each manufacturing date. These are displayed in the form of tables, or in the form of graphs.

In this analysis system, in addition to inputting chemical process parameters required to perform a simulation on the spreadsheet software, and displaying the results of the simulation on the spreadsheet software, process data for production facilities and product quality test data can also be displayed on the spreadsheet software. Therefore, by comparing this data, the chemical process can be analyzed, and the results can be used to predict chemical processes or design apparatus. Further, it may also be used for quality control of the production facility, management and analysis of reaction conditions, and design of chemical processes.

Further, by using this analysis system, chemical substance amounts in effluent which are required to be investigated by the Japanese law "pertaining to assessment of discharge amounts of specific chemical substances into the environment, and improvements to the control thereof", can be calculated easily and accurately using actual data.

Fourth Embodiment

A program for executing the chemical process analysis method of the aforesaid first embodiment to third embodiment, is stored on a storage medium.

Hereafter, the working examples of this invention will be described in more detail.

First Working Example

The equilibrium pH for temperature: 25° C., pressure: $1.0 \times 10^5$ Pa (1.0 bar), $H_2O$: 55.5 (mol), $FeCl_3$: 1.0 (mol) was simulated. This will now be described referring to the flowchart of FIG. 2.

[Step S1]

$H_2O$, $FeCl_3$ were input as chemical species, and temperature: 25° C., pressure: $1.0 \times 10^5$ Pa (1.0 bar), $H_2O$: 55.5 (mol), $FeCl_3$: 1.0 (mol) were input as chemical process conditions.

[Step S2]

The following chemical model was selected and extracted. The extracted chemical model is shown below.
; *INPUT*
INPUT:7
H2OIN:Water:H2O:18.015341
FECL3IN:Iron(III) chloride:FeCl3:162.205994
FECL3.6H2OIN:Iron(III) chloride hexahydrate: FeCl3.6H2O:270.298035
FECL3.2H2OIN:Iron(III) chloride dihydrate:FeCl3.2H2O: 198.236679

FECL3.2.5H2OIN:Iron(III) chloride 2.5 hydrate: FeCl3.2.5H2O:207.244354
HCLIN:Hydrogen chloride: HCl:36.460972
FEIIIOH3IN:Iron(III) hydroxide:Fe(OH)3:106.869110
;
; *SPECIES*
;
SPECIES:22
H2O:Water:H2O:18.015341
FECL3AQ:Iron(III) chloride:FeCl3:162.205994
HCLAQ:Hydrogen chloride:HCl:36.460972
FEIIIOH3AQ:Iron(III) hydroxide:Fe(OH)3:106.869110
HION:Hydrogen ion(+1):H+1:1.007970
OHION:Hydroxide ion(-1):OH-1:17.007370
FEIIICLION:Iron(III) monochloride ion(+2):FeCl2+2: 91.300003
FEIII2OH2ION:Diiron(III) dihydroxide ion(+4): Fe2 (OH)2+4:145.708740
FEIIICL4ION:Iron(III) tetrachloride ion(-1):FeCl4-1: 197.658997
FEIIIOH4ION:Iron(III) tetrahydroxide ion(-1):Fe(OH)4-1: 123.876480
FEIIICL2ION:Iron(III) dichloride ion(+1):FeCl2+1: 126.752998
FEIIIOH2ION:Iron(III) dihydroxide ion(+1):Fe(OH)2+1: 89.861740
CLION:Chloride ion(-1):Cl-1:35.452999
FEIIION:Iron ion(+3):Fe+3:55.847000
FEIIIOHION:Iron (III) monohydroxide ion(+2):FeOH+2: 72.854370
H2OVAP:Water:H2O:18.015341
HCLVAP:Hydrogen chloride:HCl:36.460972
FECL3.6H2O:Iron(III) chloride hexahydrate:FeC13.6H2O: 270.298035
FECL3.2H2O:Iron (III) chloride dihydrate:FeCl3.2H2O: 198.236679
FECL3.2.5H2O:Iron (III) chloride2.5 hydrate: FeC13.2.5H2O:207.244354
FECL3PPT:Iron (III) chloride:FeCl3:162.205994
FEIIIOH3PPT:Iron (III) hydroxide:Fe(OH)3:106.869110
;
; *SOLID SCALING TENDENCY*
;
SOLIDS
ALL
;
; *EQUILIBRIUM EQUATIONS*
;
EQUILIBRIUM
H2O=HION+OHION
FECL3AQ=FEIIICL2ION+CLION
HCLAQ=HION+CLION
FEIIIOH3AQ=FEIIIOH2ION+OHION
FEIIICLION=FEIIIION+CLION
FEIII2OH2ION=2FEIIIION+2OHION
FEIIICL4ION=FECL3AQ+CLION
FEIIIOH4ION=FEIIIOH3AQ+OHION
FEIIICL2ION=FEIIICLION+CLION
FEIIOH2ION=FETIOHION+OHION
FEIIIOHION=FEIIIION+OHION
H2OVAP=H2O
HCLVAP=HCLAQ
FECL3.6H2O=FEIIIION+3CLION+6H2O
FECL3.2H2O=FEIIIION+3CLION+2H2O
FECL3.2.5H2O=FEIIIION+3CLION+2.5H2O
FECL3PPT=FEIIIION+3CLION
FEIIIOH3PPT=FETIIION+3OHION
;
; *REDOX*
;
; *EQUATIONS*
;
EQUATIONS
;
; *KINETICS*
;
; *REGRESSION*
;
; *EXCHANGE*
;
; *BIOREACTION*
;
; *COPRECIPITATION*
;
END

[Steps S3–7]

Thermodynamic property data was generated based on the chemical model extracted in the step S2 (Step S3), and stored (Step S4).

Next, the chemical composition of the reaction system was determined based on the thermodynamic property data, and the equilibrium pH was calculated (Step S5). A simulation was performed on the spreadsheet software 1 (Step S6). A graph shown in FIG. 5 was displayed on the spreadsheet software 1 (Step S7).

Figure 5:
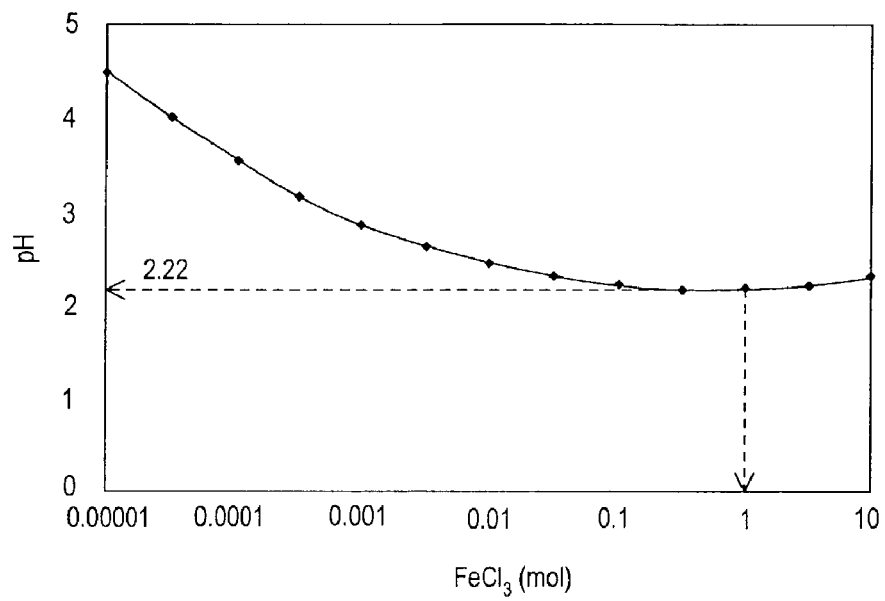
FIG. 5 is a graph showing the relation of iron chloride concentration and pH displayed on a spreadsheet software in a first working example.

From the results of FIG. 5, it was found that the equilibrium pH is 2.2.

[Comparison Between Plant Test Measurements and Analysis Results]

Figure 6:
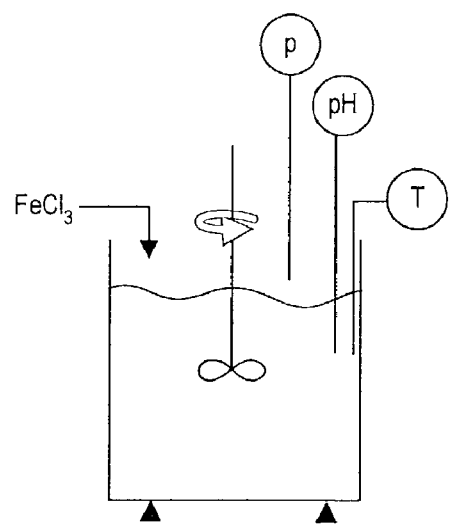
FIG. 6 is a schematic view of the apparatus used in a plant test of the first working example.

A reaction using this chemical model was performed in a real plant, as shown in FIG. 6.

In this process, pure water was first introduced into a batch process dissolution tank, and $FeCl_3$ was added. The amount of added $FeCl_3$ can be calculated by measuring the mass of the dissolution tank by a load cell. The pH, temperature and pressure (atmospheric pressure) in the dissolution tank can be measured respectively by a pH meter, thermometer and manometer inserted in the tank.

The data for this process was displayed on the spreadsheet software 1, and an analysis was simultaneously performed to determine the pH from the added $FeCl_3$ amount, temperature and pressure.

Comparing the pH measured by the pH meter and the analysis value, the observed pH is a larger value than the analysis value in the initial addition stage, and the deviation between the observed value and analysis value became constant to some extent as addition was continued.

After the experiment, when the pH meter was calibrated, it was found that this deviation was the calibration error of the pH meter. In other words, the analysis value was different from the observed value, but the analysis did proceed accurately. In an actual process, a discrepancy may occur between the analysis value (theoretical value) and the observed value, and this is often a problem of measurement as in this example.

Second Working Example

The partial pressures of $CO_2$, $H_2S$ and $NH_3$ for $CO_2$: 0.42–1.6 mol, $H_2S$: 0.04–0.4 mol, $NH_3$: 1.10–2.2 mol were simulated at temperatures of 20° C. and 60° C., and the results of the simulation were compared with experimental values. Hereafter, this will be described referring to the flowchart of FIG. 2.

[Step S1]

As parameters, $CO_2$, $H_2S$ and $NH_3$ were input as chemical species, and $CO_2$: 0.42–1.6 mol, $H_2S$: 0.04–0.4 mol, $NH_3$: 1.10–2.2 mol, temperature: 20° C., 60°
H2F2AQ=2HFAQ C. were input as the chemical process conditions.

[Step S2]

The following chemical model was selected and extracted. The extracted chemical model is shown below.

```
; *INPUT*
;
INPUT:12
H2OIN:Water:H2O:18.015341
CO2IN:Carbon dioxide:CO2:44.009899
H2SIN:Hydrogen sulfide:H2S:34.081940
NH31N:Ammonia:NH3:17.030609
H2CO3IN:Carbonic acid:H2CO3:62.025242
NH4OHIN:Ammonium hydroxide:NH4OH:35.045952
NH4HSIN:Ammonium bisulfide:NH4HS:51.112549
NH4HCO3IN:Ammonium bicarbonate:NH4HCO3:
    79.055847
NH44H2CO33IN:Ammonium
sesquicarbonate:(NH4)2CO3.2NH4HCO3:254.198166
NH42SIN:Ammonium sulfide:(NH4)2S:68.143158
NH42CO3IN:Ammonium carbonate:(NH4)2CO3:
    96.086456
HNH2CO2IN:Carbamic acid:CH3NO2:61.040508
;
; *SPECIES*
;
SPECIES: 19
H2O:Water:H2O:18.015341
CO2AQ:Carbon dioxide:CO2:44.009899
H2SAQ:Hydrogen sulfide:H2S:34.081940
NH3AQ:Ammonia:NH3:17.030609
HION:Hydrogen ion(+1):H+1:1.007970
OHION:Hydroxide ion(-1):OH-1:17.007370
HCO3ION:Bicarbonate ion(-1):HCO3-1:61.017269
CO3ION:Carbonate ion(-2):CO3-2:60.009300
SION:Sulfide ion(-2):S-2:32.066002
HSION:Hydrogen sulfide ion (-1):HS-1:33.073971
NH4ION:Ammonium ion(+1):NH4+1:18.038580
NH2CO2ION:Carbamate ion(-1):NH2CO2-1:60.032539
H2OVAP:Water:H2O:18.015341
CO2VAP:Carbon dioxide:CO2:44.009899
H2SVAP:Hydrogen sulfide:H2S:34.081940
NH3VAP:Ammonia:NH3:17.030609
NH4HSPPT:Ammonium bisulfide:NH4HS:51.112549
NH4HCO3PPT:Ammonium bicarbonate:NH4HCO3:
    79.055847
NH44H2CO33PPT:Ammonium
sesquicarbonate:(NH4)2CO3.2NH4HCO3:254.198166
;
; *SOLID SCALING TENDENCY*
;
SOLIDS
ALL
;
; *EQUILIBRIUM EQUATIONS*
;
EQUILIBRIUM
H2O=HION+OHION
CO2AQ+H2O=HION+HCO3ION
H2SAQ=HION+HSION
NH3AQ+H2O=NH4ION+OHION
HCO3ION=HION+CO3ION
HSION=HION+SION
NH2CO2ION+H2O=NH3AQ+HCO3ION
H2OVAP=H2O
CO2VAP=CO2AQ
H2SVAP=H2SAQ
NH3VAP=NH3AQ
NH4HSPPT=NH4ION+HSION
NH4HCO3PPT=NH4ION+HCO3ION
NH44H2CO33PPT=4NH4ION+2HCO3ION+CO3ION
;
; REDOX*
;
;
; *EQUATIONS*
;
EQUATIONS
;
; *KINETICS*
;
;
; *REGRESSION*;
;
;
; *EXCHANGE*
;
;
; *BIOREACTION*
;
;
; *COPRECIPITATION*
;
END
```

[Step S3–7]

Thermodynamic property data was generated from the chemical model extracted in the step S2 (Steps S3, S4).

Next, the chemical composition of the reaction system was determined, and the partial pressure of each component was calculated (Step S5).

Figure 7:
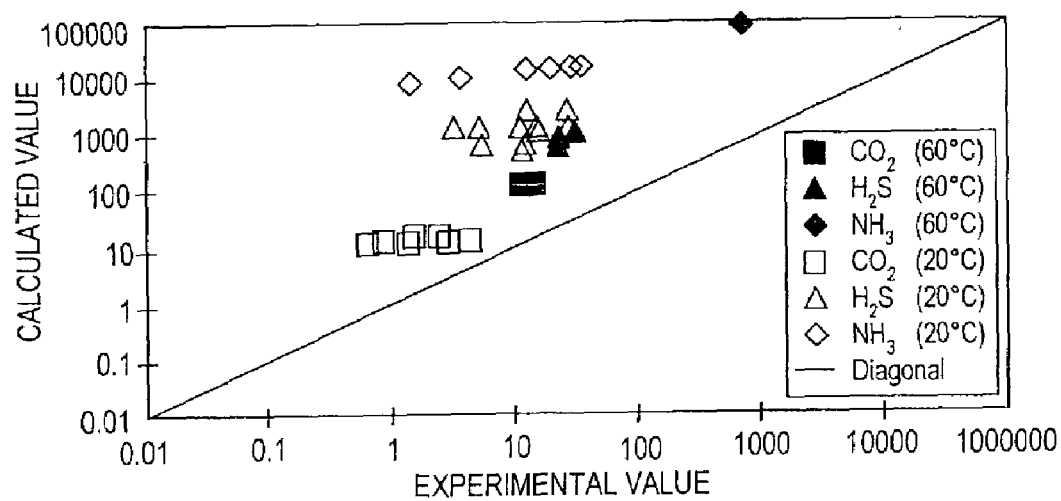
FIG. 7 is a diagram showing a relation between calculated values and measurement results displayed on the spreadsheet software when partial pressures of components are calculated using Henry's Law in a second working example.
Figure 8:
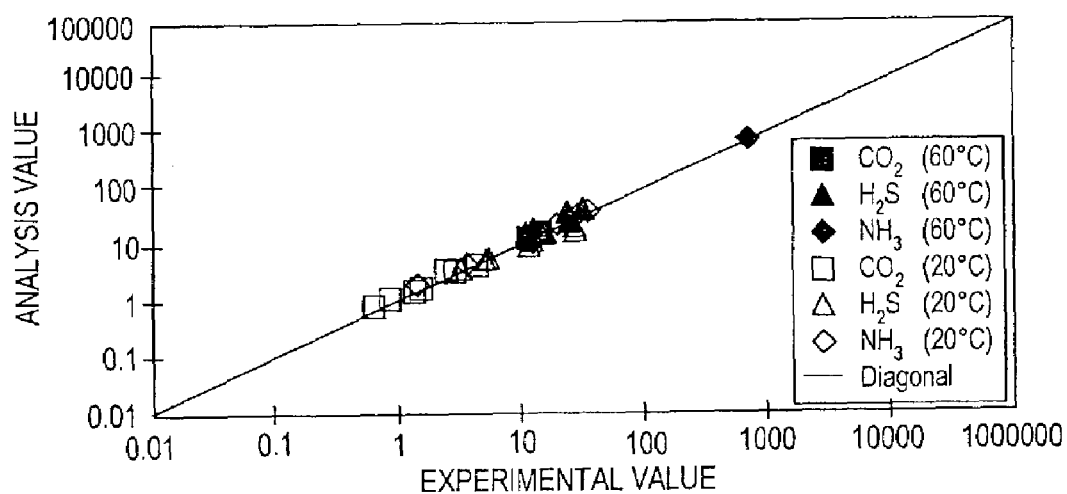
FIG. 8 is a diagram showing a relation between analysis values and experimental values displayed on the spreadsheet software when partial pressures of components are simulated by the chemical process analysis method of this invention in the second working example.

Next, a simulation was performed on the spreadsheet software 1 (Step S6), and graphs shown in FIG. 7 and FIG. 8 were displayed on the spreadsheet software 1 (Step S7).

FIG. 7 is a graph which compares calculated values according to Henry's Law, and experimental values. FIG. 8 is a graph which compares analysis values according to the analysis method of this invention, and experimental values. In both of these graphs, there is a closer approximation to the experimental values the closer the plotted data is to a diagonal line L.

From FIG. 7 and FIG. 8, it is seen that in the analytical method of this invention, experimental values and analysis results agree well, whereas when Henry's Law is used, there is a large discrepancy between the experimental values and calculated values. Hence, a more precise analysis can be performed by using the analysis method of this invention.

Third Working Example

The relation between a potassium fluoride (KF) amount generated in an evaporator and the pressure in the evaporator was analyzed using the analysis method of this invention.

Figure 9:
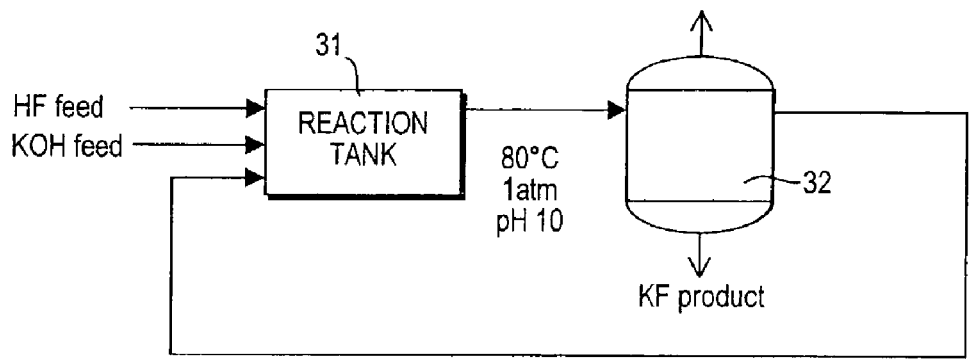
FIG. 9 is a schematic view of a process for manufacturing potassium fluoride according to a third working example.

FIG. 9 shows a schematic view of the process used to produce potassium fluoride.

In this process, potassium fluoride is manufactured according to the following chemical equation.

$$HF + KOH \rightarrow KF\downarrow + H_2O$$

Hydrogen fluoride and potassium hydroxide are introduced into a reaction tank 31, then the temperature of the reaction tank 31 and a temperature of an evaporator 32 are set. The reaction products from the reaction tank 31 are sent to the evaporator 32. The evaporator 32 is set to a reduced pressure state by a pressure reducing device. In the evaporator 32, the reaction products are concentrated, water is removed, KF product is removed, and the concentrated solution is recirculated to the reaction tank 31.

[Step S1]

$H_2O$, HF, KOH and KF were input as chemical species. $H_2O$: 188 kg/hour, HF: 25 kg/hour, KOH: 71 kg/hour, KF: 40 kg/hour, temperature: 80.0° C., pressure range in evaporator 32: $0.02 \times 10^5 - 1.0 \times 10^5 Pa$ (0.02–1.0 atm) were input as the chemical process conditions.

[Step S2]

The following chemical model was selected and extracted. The extracted chemical model is shown below.

; *INPUT*
;
INPUT:10
H2OIN:Water:H2O:18.015341
HFIN:Hydrogen fluoride:HF:20.006372
KOHIN:Potassium hydroxide:KOH:56.105671
KFIN:Potassium fluoride:KF:58.096703
H6F6IN:Hydrogen fluoride, hexamer:(HF)6:120.038239
H2F2IN:Hydrofluoride, dimer:(HF)2:40.012745
KOH.2H2OIN:Potassium hydroxide dihydrate:KOH.2H2O: 92.136353
KF.4H2OIN:Potassium fluoride tetrahydrate:KF.4H2O: 130.158066
KOH.1H2OIN:Potassium hydroxide monohydrate: KOH.1H2O:74.121010
KF.2H2OIN:Potassium fluoride dihydrate:KF.2H2O: 94.127380
; *SPECIES*
;
SPECIES:17
H2O:Water:H2O:18.015341
H2F2AQ Hydrofluoride, dimer:(HF)2:40.012745
HFAQ:Hydrogen fluoride:HF:20.006372
HION:Hydrogen ion(+1):H+1:1.007970
OHION:Hydroxide ion (−1):OH−1:17.007370
FION:Fluoride ion (−1):F−1:18.998404
HF2ION:Hydrogen difluoride ion(−1):HF2-1:39.004776
KION:Potassium ion(+1):K+1:39.098301
H2OVAP:Water:H2O:18.015341
H2F2VAP:Hydrofluoride,dimer:(HF)2:40.012745
HFVAP:Hydrogen fluoride:HF:20.006372
KOHPPT:Potassium hydroxide:KOH:56.105671
KOH.2H2O:Potassium hydroxide dihydrate:KOH.2H2O: 92.136353
KF.4H2O:Potassium fluoride tetrahydrate:KF.4H2O: 130.158066
KOH.1H2O:Potassium hydroxide monohydrate: KOH.1H2O:74.121010
KF.2H2O:Potassium fluoride dihydrate:KF.2H2O: 94.127380
KFPPT:Potassium fluoride:KF:58.096703
;
; *SOLID SCALING TENDENCY*
;
SOLIDS
ALL
;
; *EQUILIBRIUM EQUATIONS*
;
EQUILIBRIUM
H2O=HION+OHION
H2F2AQ=2HFAQ
HFAQ=HION+FION
GEN HF2ION=FION+HFAQ
H2OVAP=H2O
H2F2VAP=H2F2AQ
HFVAP=HFAQ
KOHPPT=KION+OHION
KOH.2H2O=KION+OHION+2H2O
KF.4H2O=KION+FION+4H2O
KOH.1H2O=KION+OHION+1H2O
KF.2H2O=KION+FION+2H2O
KFPPT=KION+FION
;
; *REDOX*
;
;
; *EQUATIONS*
;
EQUATIONS
;
; *KINETICS*
;
;
; *REGRESSION*
;
;
; *EXCHANGE*
;
;
; *BIOREACTION*
;
;
; *COPRECIPITATION*
;
END

[Step S3–7]

Thermodynamic property data were generated from the chemical model extracted in the step S2, and stored (Steps S3, S4).

Next, the composition of the mixture in the evaporator 32 and thermodynamic properties were calculated (Step S5). A simulation was performed on the spreadsheet software 1 (Step S6). A graph shown in FIG. 10 was displayed on the spreadsheet software 1 (Step S7).

Figure 10:
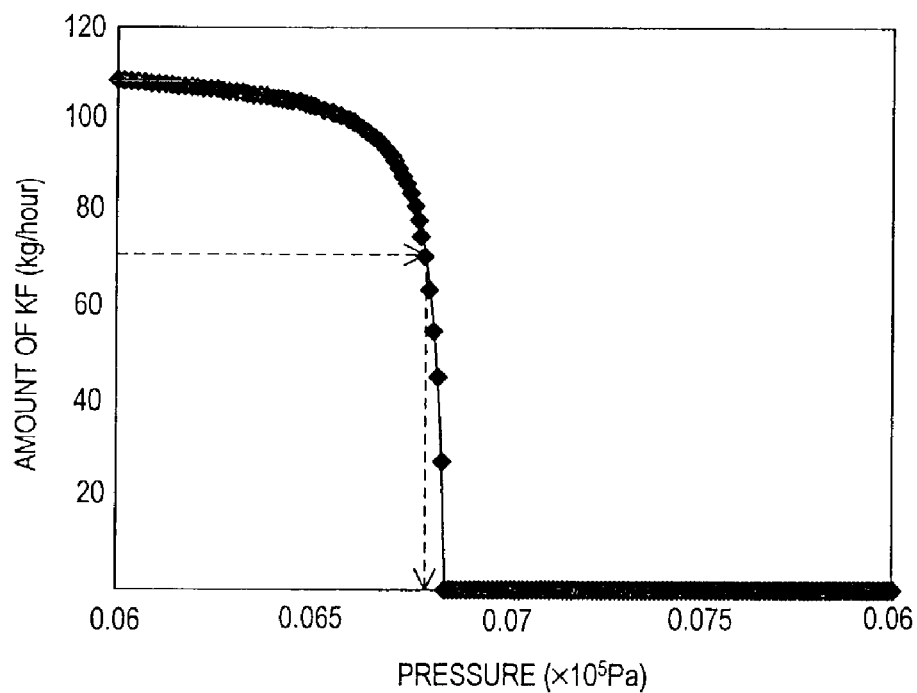
FIG. 10 is a diagram showing a relation between an amount of potassium fluoride and pressure in an evaporator displayed on the spreadsheet software according to a third working example.

As shown in FIG. 10, if the pressure in the evaporator 32 is reduced slightly below a certain value, the generation amount of KF is stable.

Industrial Field

As described above, in the chemical process analysis method of this invention, chemical process parameters are input on a spreadsheet software, and the results of a simulation of the chemical process are displayed on this spreadsheet software based on these parameters. This is useful to predict chemical processes and design apparatus from the simulation results.

Process data for manufacturing facilities and product test results are also displayed on the spreadsheet software and compared with the simulation results which is useful for making deductions.

The invention claimed is:

1. A chemical process analysis method comprising the steps of:
   inputting a chemical process condition and chemical species on a spreadsheet software (1),
   evaluating a chemical equilibrium based on the input chemical process condition and chemical species by a software (4, 6) different from the spreadsheet software (1),
   simulating the chemical equilibrium on the spreadsheet software (1) based on the evaluation results, and
   displaying the results of the simulation on the spreadsheet software (1).

2. A chemical process analysis method as defined in claim 1, wherein:
   the step for evaluating the chemical equilibrium is performed, using the other software (4,6) different from the spreadsheet software (1), by computing a characteristic value, determining an equilibrium condition and determining the chemical composition of the reaction system based on the input chemical process condition and chemical species.

3. A chemical process analysis method as defined in claim 1, wherein:
   the step for evaluating the chemical equilibrium is performed, using the other software (4, 6) different from the spreadsheet software (1), by:
   selecting and extracting a chemical model based on all chemical reactions induced by the input chemical species, and all chemical substances including intermediates resulting therefrom,
   supplying a basic condition to the chemical model, and extracting thermodynamic property data of the chemical model, and
   computing a characteristic value, determining an equilibrium condition and determining the chemical composition of the reaction system based on the input chemical process condition and extracted thermodynamic property data.

4. A chemical process analysis method as defined in claim 3, further comprising a step for storing the thermodynamic property data of the chemical model.

5. A chemical process analysis method as defined in any of claims 1–3, wherein:
   the input chemical process condition is one of a concentration condition, a temperature condition, a pressure condition, a pH condition, a bubble point, an enthalpy, a dew point and a solubility limit.

6. A chemical process analysis method as defined in any of claims 1–3, wherein:
   the input chemical species are the initial chemical species comprising the chemical model.

7. A chemical process analysis method as defined in any of claims 1–3, further comprising the steps of:
   storing process data of a production facility, and
   displaying the stored process data on the spreadsheet software (1).

8. A chemical process analysis method as defined in any of claims 1–3, further comprising the steps of:
   storing a test result for either of a manufactured product and an intermediate product, and
   displaying the stored test result on the spreadsheet software (1).

9. A chemical process analysis system comprising:
   means for inputting a chemical process condition and chemical species on a spreadsheet software (1),
   means for evaluating a chemical equilibrium based on the input chemical process condition and chemical species by a software (4, 6) different from the spreadsheet software (1),
   means for simulating the chemical equilibrium on the spreadsheet software (1) based on the evaluation results, and
   means for displaying the results of the simulation on the spreadsheet software (1).

10. A program storage device readable by a machine, tangibly embodying a program of instructions executable by the machine to perform method steps for a chemical process analysis, said method steps comprising:
   inputting a chemical process condition and chemical species on a spreadsheet software (1),
   evaluating a chemical equilibrium based on the input chemical process condition and chemical species by a software (4, 6) different from the spreadsheet software (1),
   simulating the chemical equilibrium on the spreadsheet software (1) based on the evaluation results, and
   displaying the results of the simulation on the spreadsheet software (1).

* * * * *